US006752963B2

(12) United States Patent
Dickopf et al.

(10) Patent No.: US 6,752,963 B2
(45) Date of Patent: Jun. 22, 2004

(54) SPR SENSOR SYSTEM

(75) Inventors: Stefan Dickopf, Heidelberg (DE); Kristina Schmidt, Heidelberg (DE); Dirk Vetter, Heidelberg (DE); Klaus Burkert, Heidelberg (DE)

(73) Assignee: Graffinity Pharmaceutical Design GmbH, Heidelberg (DE)

( * ) Notice: Subject to any disclaimer, the term of this patent is extended or adjusted under 35 U.S.C. 154(b) by 520 days.

(21) Appl. No.: 09/789,015

(22) Filed: Feb. 21, 2001

(65) Prior Publication Data

US 2001/0026943 A1 Oct. 4, 2001

(30) Foreign Application Priority Data

Feb. 22, 2000 (DE) .......................................... 100 08 006
Oct. 20, 2000 (DE) .......................................... 100 52 165

(51) Int. Cl.[7] .............................................. G01N 21/55
(52) U.S. Cl. .................................... 422/82.09; 356/445
(58) Field of Search .......................... 422/82.05, 82.06, 422/82.09; 356/445, 318

(56) References Cited

U.S. PATENT DOCUMENTS

| | | | |
|---|---|---|---|
| 5,313,264 A | 5/1994 | Ivarsson et al. | |
| 5,485,277 A | 1/1996 | Foster | |
| 5,792,667 A | 8/1998 | Florin et al. | |
| 5,858,799 A | 1/1999 | Yee et al. | |
| 5,917,607 A | 6/1999 | Naya | |
| 5,999,262 A | 12/1999 | Dobschal et al. | |
| 6,285,020 B1 * | 9/2001 | Kim et al. | 250/216 |
| 2002/0056816 A1 * | 5/2002 | Stark | 250/493.1 |
| 2003/0128364 A1 * | 7/2003 | Dickopf et al. | 356/445 |

FOREIGN PATENT DOCUMENTS

| | | |
|---|---|---|
| DE | 198 14 811 C1 | 8/1999 |
| DE | 199 230 820 A1 | 1/2000 |
| DE | 199 55 556 A1 | 6/2000 |
| EP | 0 286 195 A2 | 10/1988 |
| EP | 0 341 928 A1 | 11/1989 |
| EP | 0 971 226 A1 | 1/2000 |
| EP | 0 973 023 A1 | 1/2000 |
| WO | 90/05295 A1 | 5/1990 |
| WO | 95/22754 | 8/1995 |
| WO | 97/15819 | 5/1997 |
| WO | 99/30135 | 6/1999 |
| WO | 99/41594 A1 | 8/1999 |
| WO | 99/60382 | 11/1999 |
| WO | 00/31515 A1 | 6/2000 |

* cited by examiner

*Primary Examiner*—Jeffrey R. Snay
(74) *Attorney, Agent, or Firm*—Nath & Associates PLLC; Gary M. Nath; Marvin C. Berkowitz

(57) ABSTRACT

The invention relates to an SPR sensor array comprising a plurality of SPR sensor surface areas (120) arranged on a substrate (10, 20) in a two-dimensional matrix located in a plane to which the SPR sensor surface areas (120) are parallel and whereby radiation capable of exciting surface plasmons in the SPR sensor surface areas (120) under specific physical conditions can be guided through the substrate (10, 20) to be reflected from the SPR sensor surface areas, as well as separating means (110) for separating each SPR sensor surface area (120) from its neighboring SPR sensor surface area (120), wherein the separating means (110) and SPR sensor surface areas (120) are provided such that at least outside of surface plasmon resonance occurring in the SPR sensor surface areas (120) the radiation (40) guided through the substrate (10, 20) is reflected in the region of the separating means to a different degree than in the region of the SPR sensor surface areas (120) to create a contrast between the separating means (110) and the SPR sensor surface areas (120) at least outside of surface plasmon resonance occurring in the SPR sensor surface areas (120) in the radiation reflected by the SPR sensor surface areas (120) and the separating means (110).

70 Claims, 10 Drawing Sheets

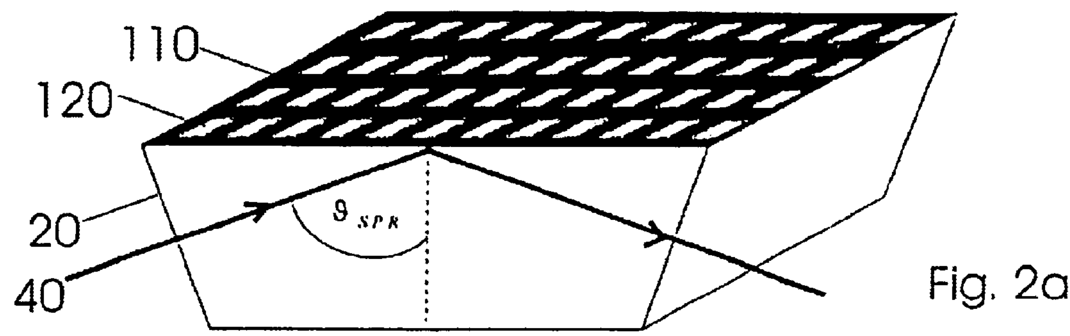
Fig. 2a
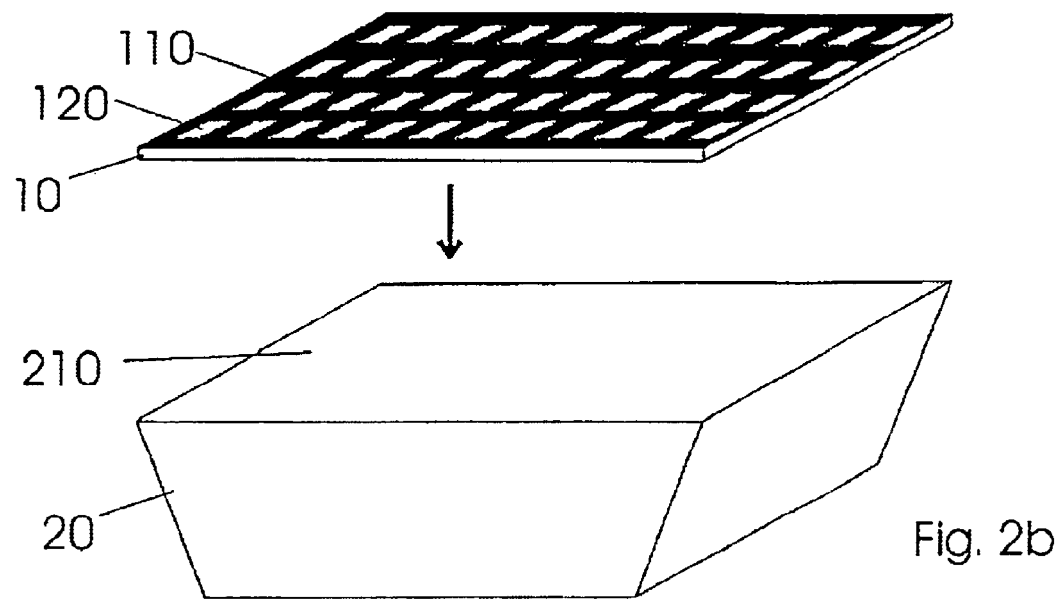
Fig. 2b
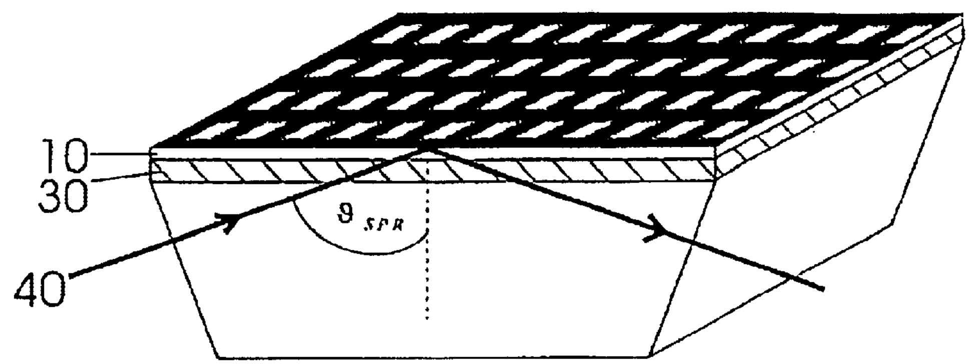
Fig. 2c
Fig. 2

Fig. 9a
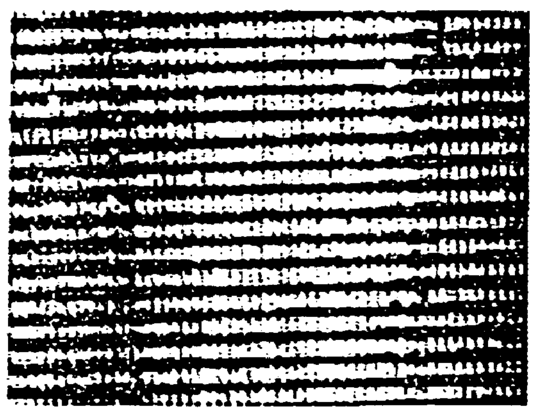
Fig. 9b
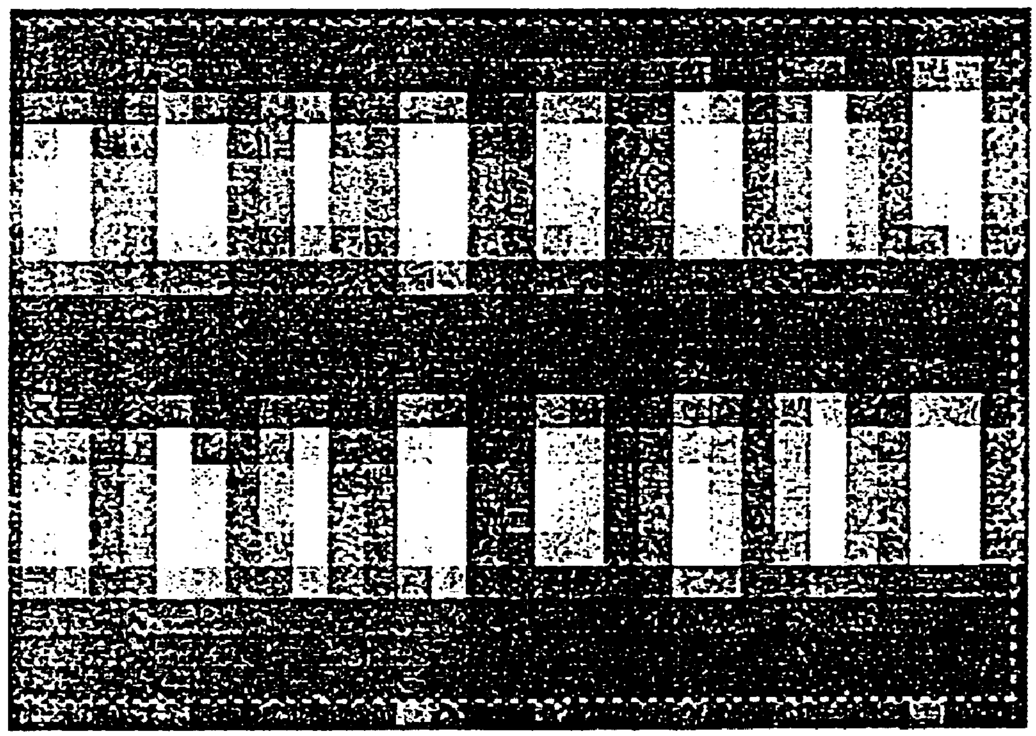
Fig. 9

SPR SENSOR SYSTEM

FIELD OF THE INVENTION

The present invention relates to providing a SPR sensor array capable of simultaneously sensing a plurality of samples, to methods for its production, measurement assemblies as well as to adjustment and measurement methods for parallel readout of the sensor system and to use thereof in the search for active substances and in high-throughput screening.

BACKGROUND OF THE INVENTION

One modern approach in the search for active substances involves generating a large number of diverse chemical compounds by means of automated synthesizers, this plurality of diverse structures then being tested for binding to interaction partners often represented by biomacromolecules such as proteins. One automated method which assays a large number of samples in this way is also termed high-throughput screening.

Due to the biological dispersion of the results in studying the bindings it is particularly important to achieve exactly the same conditions for all compounds in the binding test. This is why the test ideally should be implemented for all samples simultaneously, where possible, and with the same solution of the interaction partner under test to eliminate the effects of ageing and temperature drift as well as differences in the binding times for the compounds. Due to complexities involved in purifying biomacromolecules the quantities needed for the test should be kept to a minimum.

One particularly effective method of implementing the binding test is surface plasmon resonance (SPR) spectroscopy. Unlike fluorescence and chemiluminescence methods no dye-marked samples and also no antibodies are needed in SPR for the protein to be tested. In SPR an interaction partner (e.g. ligand) is immobilized on a metal surface and its binding to another interaction partner (e.g. receptor) demonstrated. For this purpose an optical substrate (usually a prism) is coated with gold and the drop in internal reflectivity in the prism detected as a function of the set angle or as a function of the wavelength (Kretschmann configuration). What is demonstrated ultimately is a change in the refractive index of the medium at the side opposite the gold film which occurs when molecules bind to the surface.

Figure 1A:
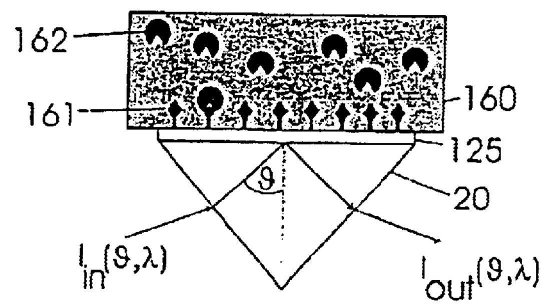

FIG. 1*a* shows diagrammatically the so-called Kretschmann geometry which is often used to measure the SPR effect. In this case a thin gold film 125 applied to a prism 20 is brought into wetting contact with the solution 160 to be assayed. What is usually measured is the internal reflectivity at glass/gold/fluid interfaces either as a function of the angle of incidence $\partial$ or as a function of the wavelength $\lambda$. At a suitable resonance condition the reflectivity is greatly reduced, the energy of the light then being converted into electron charge density waves (plasmons) along the gold/fluid interface. The condition for resonance approximates (from Chapter 4, "Surface Plasmon Resonance" in G. Ramsay, Commercial Biosensors, John Wiley & Sons (1998) ) to:

$$\frac{2\pi}{\lambda} n_{prism} \sin\vartheta \approx \frac{2\pi}{\lambda} \sqrt{\frac{n_{metal}^2(\lambda) n_{sample}^2}{n_{metal}^2(\lambda) + n_{sample}^2}}$$

where $n_{prism}$ is the refractive index of the prism, $n_{metal}$ the complex refractive index of the metal coating and $n_{sample}$ that of the sample. $\partial$ and $\lambda$ stand for the angle of incidence and wavelength of the incident light, respectively. The wavelength spectra (FIG. 1*b*) respectively the angle spectra (FIG. 1*c*) exhibit a reduction in reflectivity in the wavelength range or in the angle range respectively in which the resonance condition as cited above is satisfied. Changing the refractive index in the solution $n_{sample}$ alters the resonance condition, as a result of which the resonance curves are shifted by a value which for small changes in the refractive index is linear to this change (a calibration being made, where necessary, for larger changes). Since the reflected light penetrates into the fluid only by a few 100 nm the change in the refractive index is measured locally in this range. When the target molecules (e.g. proteins) 162 in the solution bind to suitable interaction partners 161 immobilized on the surface (i.e. association and dissociation forming an equilibrium) the local concentration of the target molecule at the surface increases which can then be demonstrated as a change in the refractive index.

WO 99/60382 describes an SPR sensor capable of simultaneously sensing a plurality of samples. A measurement assembly for reading out such a SPR sensor system in parallel is disclosed in WO 00/31515. This proposes an apparatus for implementing SPR measurements on a plurality of samples in parallel which is based on the principle of wavelength measurement, but does not use a prism, but an array of sensor fingers capable of carrying another substance on each sensor finger. This array can be coated in a microtiter plate (MTP) and measured, i.e. each sensor finger is able to measure another solution. The contrast between the sensor fields and the intermediate regions is dictated by the geometry of the waveguides. In this case light passes through the array only at the regions at which a sensor field is applied, resulting in a high contrast. The disadvantage is the expense in producing the sensor fingers and their sensitiveness to physical contact as well as the relatively high sample consumption in coating.

WO 98/34098 shows sample fields on an SPR-compatible gold film applied to a prism. The contrast is determined by setting suitable resonance conditions. The disadvantage here is that the surfaces need to be very homogenous since it is only the region of the sensor surface area that shows a contrast in imaging under SPR conditions that exhibits the same layer thicknesses.

Another SPR imaging system is described in B. P. Nelson et al., Anal. Chemical 1999, 71, pages 3928–3934. In this case a uniform gold surface applied to a non-structured glass plate is patterned with an array of 500×500 $\mu$m large squares covered with DNA, the DNA squares being separated by squares covered with alkanethiol intended to prevent adsorption of the protein outside of the DNA squares. The DNA squares are then brought into contact with a protein sample and an image of the gold surface produced at the SPR angle on an CCD chip before and after contact is made. Here, distinguishing the DNA squares from the other regions depends on the molecular weight of the immobilized chemical or biological molecules, the contrast sinking with a reduction in the molecular weight. Also a disadvantage in this system is the relatively large pixel region to which a DNA square needs to be assigned on the CCD camera to ensure adequate contrast. These requirements conflict with the need for a miniaturized SPR sensor array for universal application.

Described in WO 90/05305 is a replaceable sensor unit for use in an optical biosensor system (WO 90/05295) in which the geometry and arrangement of the sample fields on the non-structured sensor unit is not dictated by the latter.

Assigning the sample fields on the sensor unit is done by bringing it into contact with a block unit for handling the fluids, e.g. the throughflow system as disclosed in WO 90/05295, the throughflow system defining the arrangement of the sensor surfaces one-dimensionally (one-dimensional array). The disadvantage in this case is that making use of a throughflow system makes it difficult to use and miniaturize a two-dimensional sample array (two-dimensional array).

OBJECT OF THE PRESENT INVENTION

The present invention is based on the object of providing an improved SPR sensor array.

SUMMARY OF THE PRESENT INVENTION

This object is achieved by the characterizing features of the claim 1 and the subject matter of parallel claims respectively. Advantageous aspects are the subject matter of the dependent claims.

In accordance with the invention separating means or separators are provided for structuring the SPR sensor array so that a two-dimensional sample array is made possible. A plurality of samples is arranged in a two-dimensional sensor array such that the geometry and number of the sensor fields or sensor surface areas as well as the contrast between sensor fields and their intermediate regions are determined by separating means on the sensor system and the surface areas of the sensor fields are located parallel to the coordinate plane of the sample array. Since the separating means create a contrast outside of surface plasmon resonance occurring in the SPR sensor surface areas, positioning and adjusting a sensor array in a measurement assembly can now be done directly in that practically any radiation can be directed to the array, permitting a setting due to the contrast produced between the SPR sensor surface areas and the separating means, since this enables these regions to be easily distinguished from each other in imaging or the individual SPR sensor surface areas to be easily distinguished from each other.

In other words, whereas in prior art as per B. P. Nelson et al. (see above) the variable physical conditions (e.g. the angle of incidence of the radiation on the sensor array or the wavelength of the radiation) needs to be regulated highly precisely to the resonance to permit distinguishing the regions to be analyzed from each other in imaging, since in this case outside of the resonance similar reflection occurred from the regions spotted with DNS and with alkanethiol on the gold, now in the present invention sensing can be done with a radiation under practically any physical condition (any angle or any wavelength) and the existing contrast permits distinguishing the regions. The molecular weight of the chemical compound to be immobilized can also be selected optionally, thus also permitting the application of small organic molecules (smaller than 5000, preferably smaller than 1000, even better smaller than 500 Dalton).

Although it is possible that the reflection in the region of the separating means outside of resonance occurring in the SPR sensor surface areas is smaller than in the region of the SPR sensor surface areas, the SPR sensor surface areas and the separating means are configured so that the reflectivity of the separating means is less than the reflectivity the SPR sensor surface areas, i.e. at least outside of resonance occurring in the SPR sensor surface areas. The absorption in the resonance range is possibly so strong that the reflectivity in these SPR sensor surface areas at resonance is less than the reflectivity of the separating means. This merely results in an inversion in the contrast in the resonance range so that distinguishing the regions in imaging continues to be possible directly. The reflection spectrum of the SPR sensor surface areas intersects the (preferably constant) reflectivity of the separating means, at two points so that it is only precisely at these points that no contrast occurs which is obviously negligible and doubtlessly a major advantageous over the system as per B. P. Nelson et al. It is, however, preferred in the present invention to configure the separating means and SPR sensor surface areas so that the reflectivity of the SPR sensor surface areas is always greater than the reflectivity of the separating means, also in the resonance range in the SPR sensor surface areas.

In one preferred embodiment the separating means are directly applied to the sensor system. Achieving the separating means and the sensor surface areas can be performed in suitable ways, it is thus being possible to apply a radiation-absorbing substance to the sensor substrate as the separating means whilst an SPR-compatible material, e.g. a metal, preferably gold, is deposited as the SPR sensor surface area. It is possible to make use of a material as the separating means which has a refractive index equal to a larger than (preferably larger by max. 0.1) than that of the substrate material so that the radiation although refracted from the substrate into the separating means does not permit refraction back into the substrate. This can also be combined with the use of an absorbing material, by introducing namely into the separating means with the higher refractive index additional radiation-absorbing substances such as e.g. carbon or a dye. Preferably the thickness and width of the layer comprising the contrast-forming material is determined so that radiation refracted from the substrate into the layer is reflected back to the substrate maximally twice at the side of the layer facing away from the substrate surface.

Suitable materials for the separating means are absorbing layers of metal or a semiconductor or polymers (e.g. photoresist, silicon).

Preferably the separating means assure in addition that no contamination between the sensor fields or SPR sensor surface areas can occur. This is achieved by the separating means forming elevations above the SPR sensor surface areas in the direction perpendicular to the substrate preferably 0.01 mm to 5 mm differing in height. It is good practice when the flanks or surfaces of the separating means forming vessels for receiving a sample fluid are hydrophobic or hydrophobicized so that an aqueous solution is well contained without the possibility of cross-contamination with other SPR sensor surface areas.

In one aspect the SPR sensor array consists of a prism coated with a SPR-compatible layer of metal, where necessary, provided with an adhesive-promoting film as well as with the separating means.

In another aspect the SPR sensor array multiply consists of a sample-carrying sensor array provided with separating means and SPR sensor surface areas and a beam-guiding component. The beam-guiding component consists preferably of a prism. In addition an optical mediator for suitably adapting the refractive index may be provided between the beam-guiding component and the sample-carrying sensor unit.

Minor inhomogenities in the thickness of the gold film (up to 2–3 nm) are acceptable in these arrays since the image of the sensor surface area is visible irrespective of SPR resonance.

In addition the invention relates to a measurement assembly containing the SPR sensor array for parallel measurement of a plurality of preferably differing samples which can be produced at low cost in many copies and thus also suitable for once-only use to thus reduce substance consumption for coating a sensor field as compared to prior art sensor systems.

For examining a plurality of differing samples for interaction by the SPR method it is good practice to arrange them on a substrate two-dimensionally (two-dimensional array) and to image them in parallel e.g. with the aid of a CCD camera. In analyzing the image recorded by such a spatial resolution detector it is an enormous advantageous that the invention produces a strong light/dark contrast between the regions spotted by the samples (sensor fields) and the intermediate regions to achieve a sharp image of the sensor fields which permits an improved assignment of the physical spatial coordinates of the samples on the substrate to the coordinates in the image.

For this purpose prior art made use of the SPR effect itself, the contrast being produced solely by setting suitable resonance conditions e.g. by setting a suitable angle for an angle-dependent measurement. Since in resonance too, the light is not totally converted into surface plasmons this method of producing the contrast is at a disadvantage as compared to the present invention (10–20% of the light is also reflected in resonance), this likewise making high demands on the homogeneity of the thickness of the gold film. Better results are obtainable by employing structured, absorbing layers, i.e. the separating means of the present invention.

Common to all approaches of the prior art as cited for parallel sensing a plurality of samples is that the contrast between the fields spotted by the samples and the intermediate regions is not dictated by contrast-generating separating means as taught by the present invention.

Figure 1:
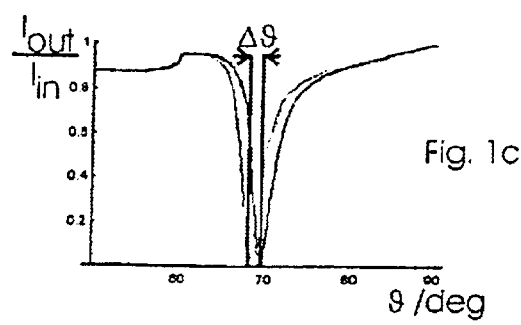
Figure 1:
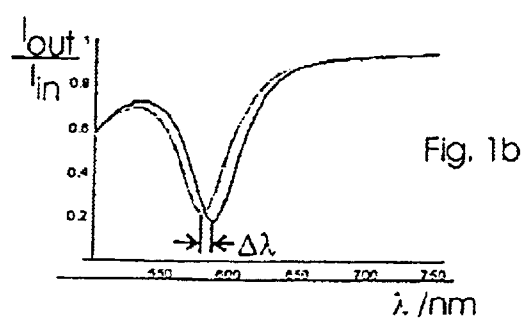
Figure 3:
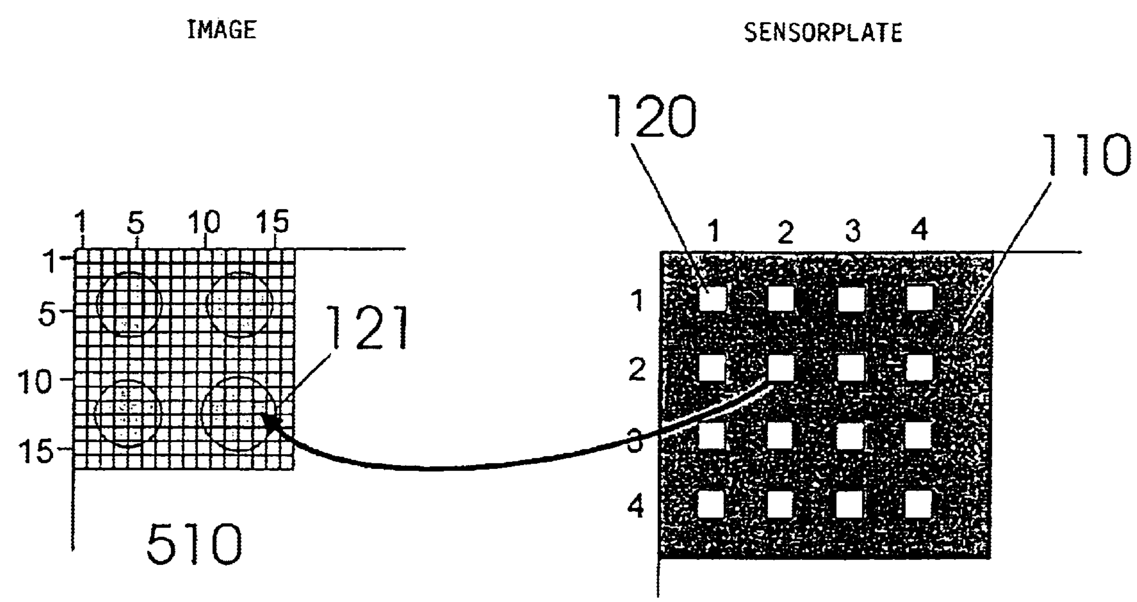
Figure 4A:
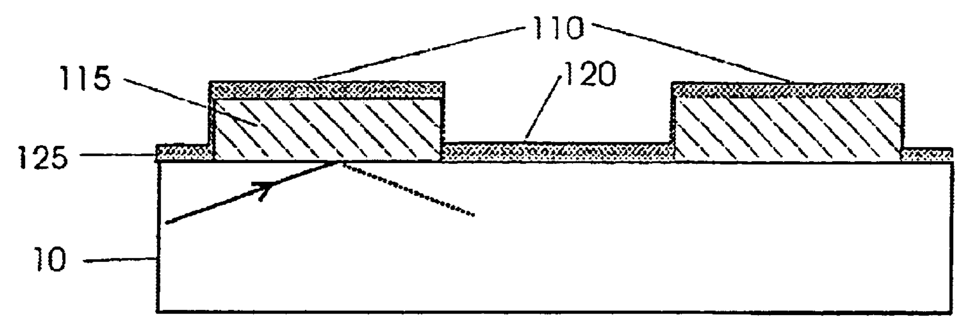
Figure 4B:
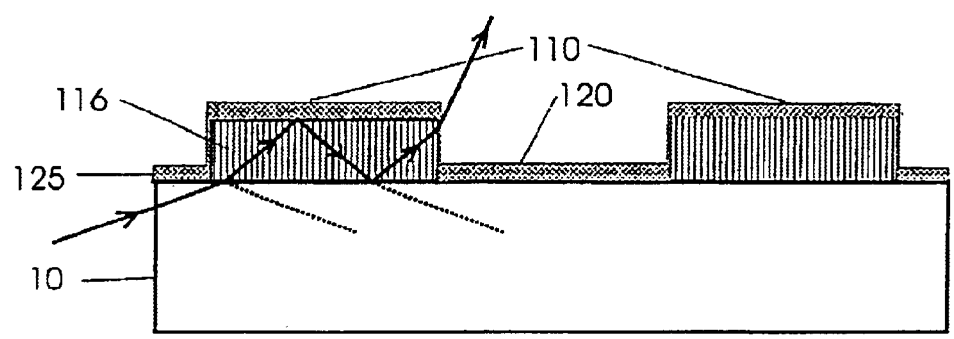
Figure 4C:
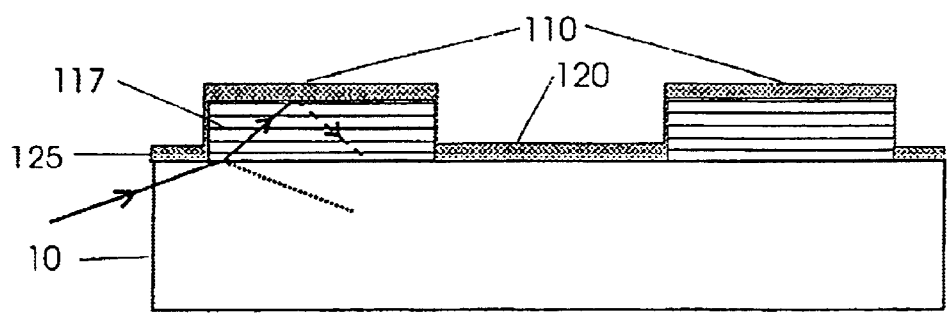
Figure 5:
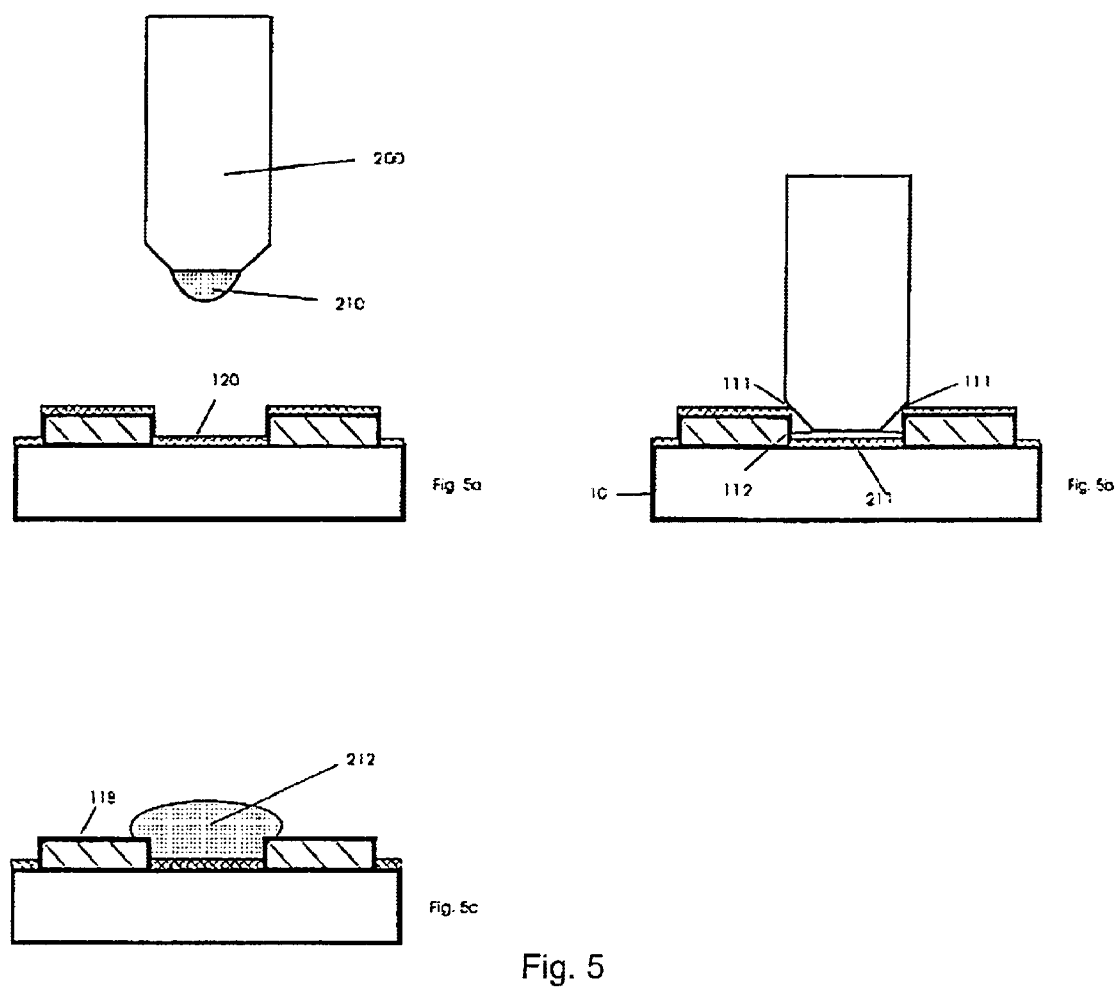
Figure 6A:
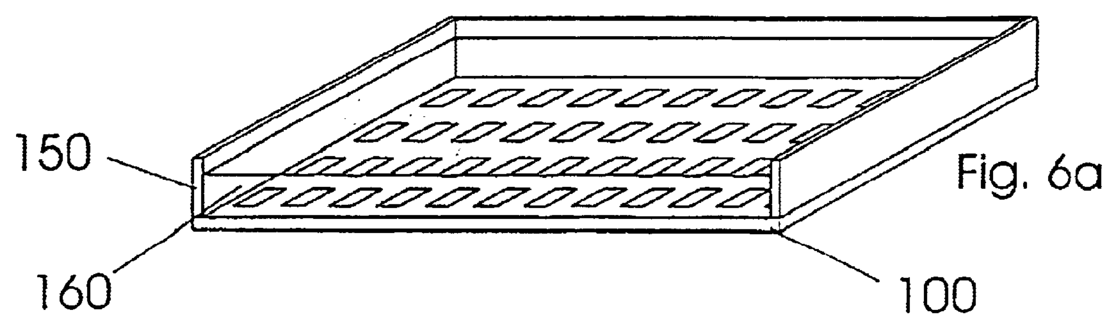
Figure 6B:
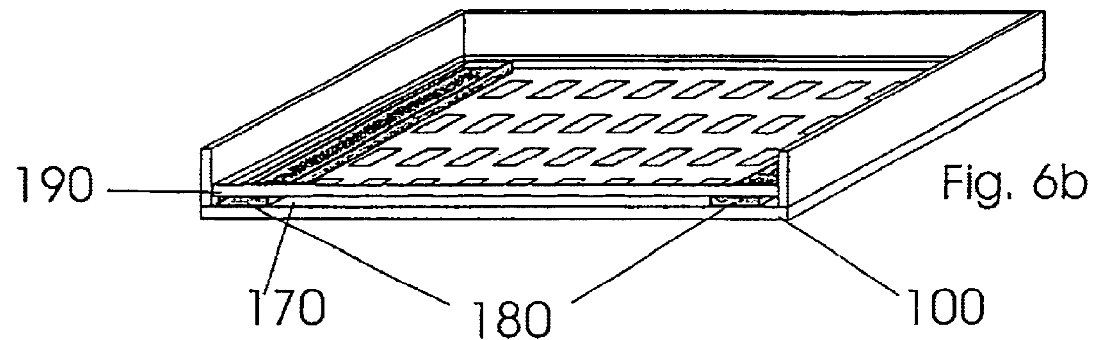
Figure 6C:
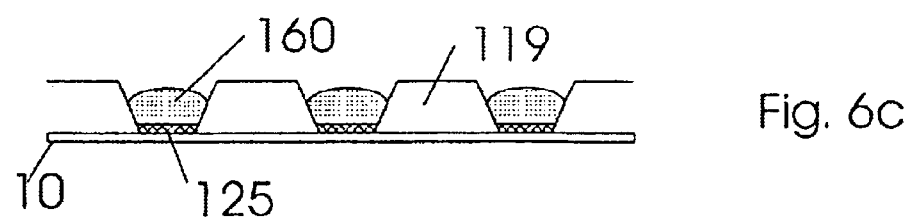
Figure 7:
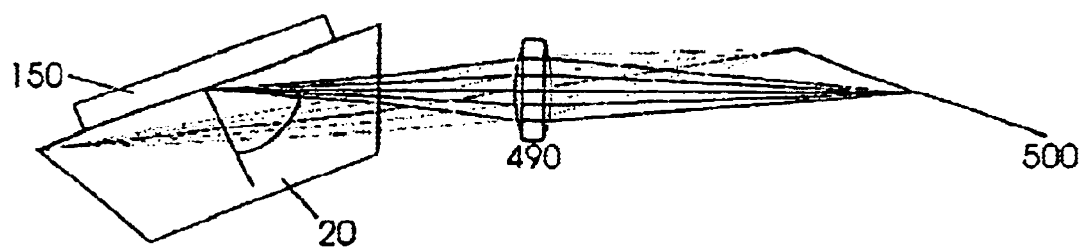
Figure 8:
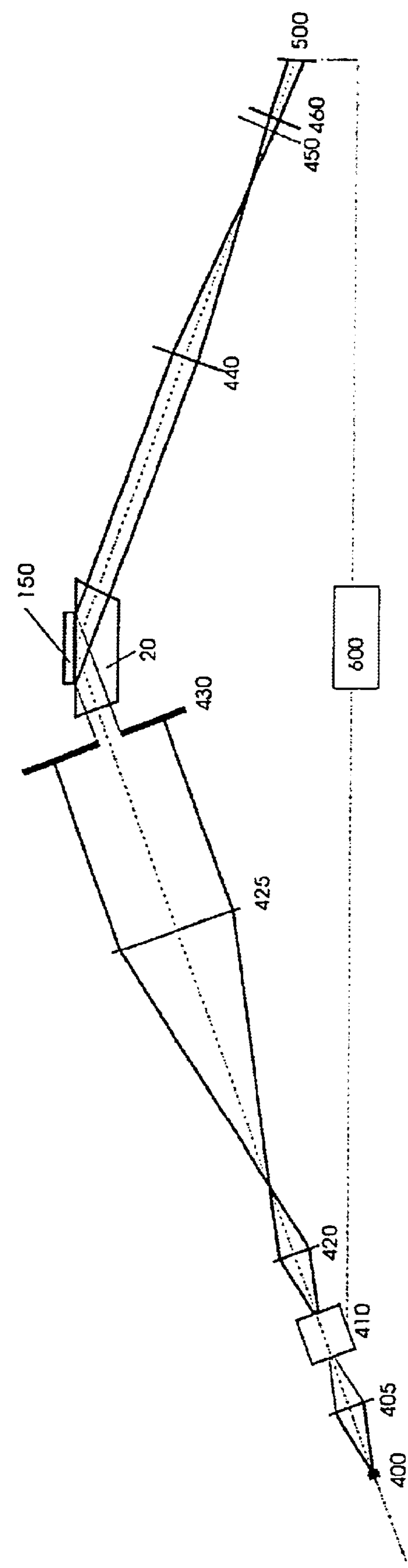
Figure 10:
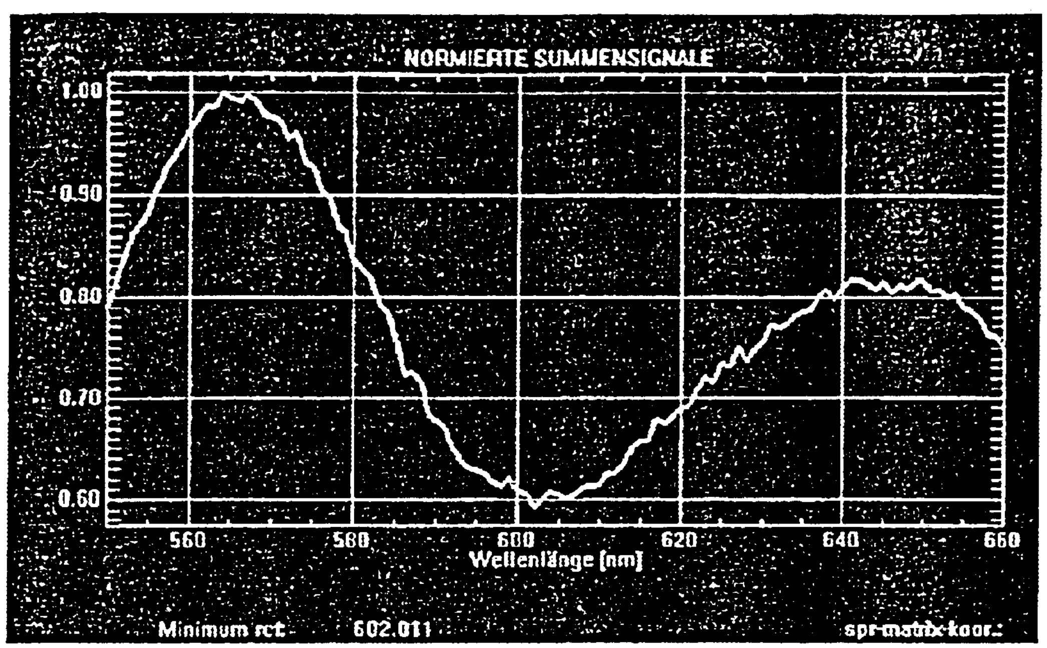

The invention will now be detailed by way of example embodiments with respect to the drawings in which:

FIG. 1 is a diagrammatical illustration of a typical Kretschmann geometry,

FIG. 2 is a diagrammatical illustration of the principle configuration of the sensor system in accordance with the invention in three embodiments, FIG. 3 illustrates the assignment of a single SPR compatible sensor element to the pixels of a CCD array, FIG. 4 illustrates three basic possibilities of eliminating light at locations in the sensor system where not desired, FIG. 5 illustrates a structure edge for guiding the fluid transfer pins, FIG. 6 illustrates a sensor system including spacers or cavitations, FIG. 7 illustrates the basic principle of the Scheimpflug method for obtaining a sharp image of the sensor field on a detector, FIG. 8 illustrates a beaming arrangement for telecentric imaging and parallel illumination in avoiding image distortions, FIG. 9 is a detail taken from the image of a sensor system and FIG. 10 is a spectrum obtained from 5 pixels.

To permit testing a plurality of samples the surface of the sensor unit carrying the samples is divided or structured into fields and on each field or sensor surface area preferably a separate sample is immobilized. Each of these fields is the detected spatially separate from the others.

A sample-carrying sensor array is advantageously put to use in the scope of the invention which is assigned samples with the aid of commercially available robotic spotters. In spotting, the samples are transferred by means of transfer pins or multipipettes from a microtiter plate to the sensor plate. For this purpose the transfer pins are dipped into the sample fluid, the droplet of which sticking to the tip of the transfer pin is then deposited on a sensor field of the biochip. By varying the pin size differing volumes of sample can be transferred.

The substance consumption for coating a sensor field by spotting techniques is in the nanoliter range as compared to approx 5 ml for a sensor finger in 1536-type MTP format as described in WO 99/60382.

Referring now to FIG. 2 there is illustrated the principle configuration of the sensor system in accordance with the invention.

For cost-effective structuring it is good practice not to structure the beam-guiding component 20 (preferably a prism) directly—as shown in FIG. 2*a*—but instead to insert a sample-carrying sensor unit 10 which is then placed on the prism—as shown in FIGS. 2*b* and 2*c*. The sensor unit consist of a planar, optically transparent substrate, preferably a structurable glass plate (also termed biochip in the following), although the plate may also be made of suitable plastics material.

In addition, it is possible to consider the biochip separate from the optical beam passage, a reader being provided for this purpose in which the optical detection path is already set and the biochip is simply placed on the prism for reading.

Separating means 110, e.g. in the form of a structurable absorbing film (resist, bonded Si, polymer and the like) is deposited on this biochip to produce the sensor fields 120.

The light enters perpendicularly into the left-hand side window of the prism. So that the light 40 irradiated under SPR conditions (i.e. so that the angle of incidence $\partial_{SPR}$ is above total reflection) is not reflected at the interface of the prism surface 210 to the air gap prior to the biochip 10 (as is usual in SPR measurements) it is brought into contact with the prism 20 with the aid of an index-matching fluid or index fluid 30. This causes the light to pass through the index fluid 30 and into the glass plate located thereabove and is first reflected by the top side coated with gold. One example of an index fluid 30 is oleic acid or a mixture containing oleic acid.

Where sample assignment of the sensor fields is done by spotting it is necessary that the fluid droplet is immobilized on the sensor field to prevent crosstalk to the neighboring field. For this purpose cavitations may be produced in the plate similar to the cavitations of a micro- or nanotiter plate.

It is understood that FIG. 2 merely shows one example of an array of SPR sensor surface areas, i.e. the sensor surface areas as shown must not necessarily be rectangular, but may be of any other shape. Thus, in some applications it is good practice when the sensor surface areas are round or oval in shape. It is also understood that not all sensor surface areas of the raster need to have the same shape and/or size, although this is to be preferred.

It is also to be noted that the illustration in FIG. 2 is merely diagrammatic. In real sensor arrays in accordance with the invention it is possible to attain sensor surface area densities of more than 10,000 sensor surface areas per $cm^2$ which is of great advantage as regards speedy, efficient measurement in which a large number of samples can be measured simultaneously in making use of minute sample volumes. In this arrangement the sensor surface area density should be at least 100, better 1000 sensor surface areas per $cm^2$, this being a further advantage of the present invention over that disclosed by the paper B. P. Nelson et al., since this is suitable only for very large sensor surface areas (squares) of 500×500 $\mu m^2$.

It is now needed to detect the intensity of the light of each gold coated sensor field 120 optically separate from neighboring fields. This is achieved by imaging the sensor surface on a spatially resolving detector. So that the sensor fields are rendered visible with good contrast on the detected image 510 (see FIG. 3) the light incident at the intermediate regions 110 needs to be absorbed, dispersed or directed away in a direction other than that of detection as best possible, it being this contrast between sensor region and edging that first permits assigning pixel regions 121 in the image 510 to a sensor field 120. During data capture the pixels of a region in the image is summed so that with good absorption of the intermediate regions 110 also the spectra for the sensor fields 120 become more informative since the underground carrying no SPR signal is minimized.

Adjusting the system is thus simple since firstly the sensor array (with or without samples on the sensor surface areas) is inserted into the measurement system and then imaging done with a radiation under any incident condition (i.e. any angle or any wavelength—see also FIG. 1), the contrast permitting distinguishing the individual sensor surface areas from each other or from the separating means.

Referring now to FIG. 4 there are illustrated a few basic possibilities of eliminating the light from locations where it is not wanted.

Evident from FIG. 4 is a structurable, absorbent layer 115 (resist, bonded Si, polymer and the like) deposited on the glass plate 10 to generate the sensor fields 120. This layer is preferably not SPR-compatible. This is followed by coating with gold 125 (or some other SPR-compatible material) so that the light at the locations 110 where the absorption layer is provided, cannot penetrate to the gold. The gold or the metal in general is deposited by means of known techniques, e.g. vapor deposition or sputtering, the absorption in this case occurring at the interface to the structured layer. It is good practice to deposit the gold film last so that it is thus least exposed to mechanical stress. This method fails to achieve, however, total absorption of the light, part of which is always reflected by the interface.

A second possibility of eliminating the light is illustrated in FIG. 4*b*. In this case a polymer 116 having the same, or somewhat higher, refractive index than that of the glass substrate 10 (e.g. 0.08) is made use of. A difference in the refractive index of 0 to 0.1 is suitable in general to thus allow the light to penetrate into the this polymer region 116 with but a low % of reflected light. Although the light is mainly reflected at the side facing the gold, it is unable to penetrate back into the glass substrate 10 with any effectiveness since the refractive index is higher and the angle is near total reflection. After being reflected once or twice within the polymer layer the light emerges at a side edge of the structured layer since the angle here is way below that of total reflection. In this arrangement the polymer layer acts as a light (arrester) conductor. What is important, however, for this basic function is to dimension the layer 116 preferably so thick that no more than one to two reflections to the glass plate 10 occur since it is here that there is always some of the light which penetrates back into the glass.

Another possibility of eliminating the light is a combination (FIG. 4*c*) of the possibilities as shown in FIG. 4*a* and FIG. 4*b*. In this case too a polymer 117 is structured to comprise a refractive index slightly above that of the glass substrate 10 (only by a few hundredths more, where possible,) so that the light enters this layer and only a few per mill are reflected. In addition in this method light-absorbing substances e.g. carbon or graphite are incorporated in the polymer material, it being this material selection that the light experiences a masking mechanism (similar to that as shown in FIG. 4*b*) intensified here, however, by the absorption of the substances in passing through the polymer. This thus achieves a significant improvement in light elimination as compared to the two methods as described above.

Referring now to FIG. 5 it is evident that structuring the layer, apart from light elimination, also provides further functions in applying the sample fluid. The edge 111 of the polymer structure serves to guide the fluid transfer pin 200 which deposits the fluid droplet 210 on the sensor field 120 (FIGS. 5*a* and 5*b*).

A further property of the grid or matrix structuring is the surface finish, the smooth hydrophobic surface of the sides 112 serving additionally to immobilize the fluid droplet 211 in preventing cross-contamination of the neighboring field. This effect can be enhanced by coating the structuring regions not with gold but e.g. with Teflon to thus create additional hydrophobic surface areas 118 (FIG. 5*c*) to permit retaining larger fluid quantities 212 than the volume of the deepening. Another possibility of creating additional hydrophobic surface areas is to hydrophobize the gold film. This is achievable, for example, by coating these regions of the gold film not forming the sensor surface, with alkylthiols forming a dense self-assembling monolayer.

Preferably the sensor fields permit arranging in a whole number fraction of an optional microtiter format to facilitate parallel transport of the sample from a microtiter plate to the sensor plate by a transfer tool, fractioning enabling sensor spacings down to a few 10 mm to be achieved. The sensor fields may be square, rectangular or round, whereby the extent in the direction of light propagation should still be sufficient so that the formation of plasmon waves is not restricted (likewise a few 10 mm). The preferred surface area range of a sensor field is $10^2$ to $10^8$ $mm^2$.

Referring now to FIG. 6 it is evident that for measurement the SPR sensor field coated with an interaction partner is brought into contact with the sample (e.g. protein solution) to be characterized. For this purpose it is good practice to apply a well 150 about the biochip (FIG. 6*a*) to permit filling with the sample fluid 160 whilst protecting from contamination with index fluid. This so-called "one-well" design of the sensor plate also makes it possible to implement all steps in preparing the gold films (cleaning, precoating, etc) in parallel.

For measurement it is sufficient to totally wet the SPR compatible metal regions with the sample to thus permit generating a capillary gap 170 over the sensor plate 100 with the aid of spacers 180 and a glass plate 190 to minimize the amount of fluid needed (FIG. 6*b*). Air inclusions in filling the capillary gap are to be avoided where possible.

The sensor plate may also be divided into partial areas by means of a structured cover plate provided with elevations and deepenings forming a capillary gap and placed on the sensor plate as disclosed e.g. by WO 99/56878 to which reference is made in its full content. These partial areas can then be filled with differing samples, filling being done by capillary action.

Possible as a further embodiment are fields having deep cavitations similar in dimension to those of microtiter plates (FIG. 6*c*) with which each sensor field can be measured with another solution 160 (MTP plate with glass-gold bottom). In this case the sensor plate consists of a gold film 125 forming the sensor surface areas on a planar substrate 10 including separating means 119, here too, a one-well structure being good practice.

One variant of producing the sensor plates (biochips) as described above consists of the possibility of producing polymers in thin films e.g. by centrifuging on a substrate. In this arrangement the polymers present in dissolved form still to cure (e.g. PMMA, polycarbonate, UV curable adhesives, photoresists or siliconized polymers (cyclotenes or ORMOCERE) are centrifuged or poured onto the glass substrate material. To obtain the absorption effect within the light-guiding layer, light-absorbing substances (e.g. graphite or dyes) are admixed in the polymer which absorb in the SPR wavelength range (e.g. for gold above 500 nm) but without influencing the photostructurability in UV. The refractive index of the polymer to be applied should be somewhat higher than that of the glass substrate so that the light-masking effect as described above occurs. In addition the refractive index of the glass substrate should be compatible with the SPR effect. When using UV curable polymers and following a uniform coating, the non-exposed regions are separated out so that sensor fields in the form of free regions remain on the glass substrate. Miniaturizing the sensor regions is thus limited only to still permitting the formation of surface plasmons. Other polymers may be produced in the desired sensor field structure (e.g. a matrix field) by screen printing, lift-off, physiochemical deposition or other replication techniques.

After structuring the sensor fields a suitable well of a plastics material is bonded in place. The complete sensor plate is then vaporized with an adhesion-promoting film as well as with an SPR-compatible gold film in obtaining the SPR-compatible sensor fields at the locations at which no polymer exists between gold and glass.

Resists (e.g. epoxy resins) can be photostructured just. the same as for polymers with UV light which are absorbent in the visible and IR range.

Required between the prism and the sensor plate is an optical mediator (preferably an index fluid) to render the sensor plate accessible to light, immersion oil typically being used for this purpose, although it is just as feasible to make use of a polymer or a gel as the optical mediator. The film of index fluid should be thicker than the coherence length of the light to avoid interference, a few 100 $\mu$m being sufficient where thermal light is concerned. Filling is preferably done by capillary action in producing a capillary gap with suitable spacers between sensor plate and prism. In this arrangement care must be take to avoid air inclusions since otherwise the region located thereabove on the sensor plate is optically inaccessible.

In principle there are several possibilities of optically reading the SPR sensor fields. In sequential scanning a light beam could scan one field after the other similar to a laser scanner in machining, although instead of this the sensor plate can also be moved on the prism with the aid of a x-y positioning table so that only one sensor field at a time is brought into the focal point of a pencil light beam.

Also possible is to proceed line-by-line in making use of a spatial resolution detector in the one spatial direction the stripe and in the second direction the wavelength or angle dependency of the spectrum is imaged. To read the array the sensor field would then need to be shifted with a positioning table through the reading line.

In addition, two-dimensionally imaging the sensor surface area on a spatially resolving detector is also possible, a new image being detected in this case for each variation of the angle or wavelength. From this series of images a spectrum is constructed for each and every sensor field for differing angles or wavelengths by forming the sum of the reflectivities over the pixel region assigned to the sensor field (the same as described in WO 00/31515). Preferably the wavelength spectrum is selected since this permits with the aid of chromatically corrected optics a stationary image (even when the wavelengths differ), whereas when detecting the spectrum as a function of the angle moving elements (goniometers) are needed which makes it much more difficult to achieve a stationary image (since the viewing angle is changed all the time). However, any drift in the sensor regions in the image 510 (see FIG. 3) can be taken into account in this angle-dependent analytical method by numerical image processing.

When attempting to arrange a two-dimensional array on the prism this sensor field must be imaged at the SPR angle $\partial_{SPR}$ (which is in the range of approx. 65° to 85° for gold) on a detector. A sharp image is obtained with the Scheimpflug method in which the object (bottom of the well 150) as well as the detector plane 500 are inclined relative to the optical axis of the imaging lens 490, the principle of which is indicated in FIG. 7. However, for one thing, this produces on the image the "falling lines" as known from photography in the direction in which the object is tilted, and for another, equidistant lines in the direction perpendicular thereto in the image to parallel lines with increasing spacing, thus making it difficult to analyse the image with a rectangular grid.

Referring now to FIG. 8 there is illustrated how these image distortions can be avoided by employing a telecentric imaging with parallel illumination (cf. WO 00/31515) in which monochromatic light is expanded and collimated (for total illumination of the sensor field) by means of a telescope comprising achromatic lenses 420 and 425. A slot aperture 430 reduces the cross-section of the beam to a rectangular shape needed for illuminating the entry window of the prism 20. The light is reflected at the SPR angle by the SPR-compatible structured bottom of the well 150 as described above. A second telescope comprising achromatic lens 440 and objective lens 460 images the SPR well bottom on a suitable scale on the CCD detector 500. So that the image is focussed over the full surface area the CCD chip is tilted relative to the optical axis. Telecentric imaging results in a likewise rectangular image on the detector from a rectangular grid on the sensor field. Due to the large SPR angle the image of the sensor plate appears in the dimension by which the object is tilted relative to the optical axis, but compressed by the factor $1/\cos(\partial_{SPR})$—see also FIG. 9. There are three ways of getting round this problem:

1. Providing the grid of the sensor field in the direction in which it is later tilted with a greater grid spacing than in the direction perpendicular thereto.
2. Compensating the distortion in the one direction by an anamorphotic objective lens 450 similar to that as used in cinematography.
3. Using a combination of 1. and 2. to achieve in all an image in which the sensor fields are sufficiently resolved in both directions of the image.

To detect the wavelength spectra the light of the light source 400 is coupled by an optical system 405 into a monochromator 410 (in FIG. 8 the basic principle is shown extended merely for the sake of a better overview which can be folded in an alternative configuration with the aid of mirrors to achieve a more compact system). The monochromator is controlled via a PC 600 which can also read the images of the CCD. For each wavelength an image is then recorded from which a reflectivity value is obtained for each sensor field by summing the results over pixel regions. Adjusting the monochromator then produces in succession a reflectivity spectrum for each sensor field which due to plasmon resonance has the profile as shown in FIG. 1*b*.

Due to the possibly of creating minute sensor surface areas and also due to it being possible to precisely calibrate or identify the sensor surface areas in spatial resolution imaging the array can be configured so that only a small number of pixels, namely less than 10, preferably five or less, is assigned to each sensor field in imaging.

EXAMPLE

FIG. 9*a* shows a detail (200×150 pixels) of an image of a sensor plate having a matrix of 562.5×1125 $\mu m^2$, as obtained with an optical assembly as described in the last paragraph. The size of the square sensor fields is 280×280 $\mu m^2$. With these dimensions approx. 12,000 sensor fields can be accommodated on the surface area of microtiter plate. Structuring the sensor plate was done with Ormocer to which graphite was admixed, the thickness of this layer being approx. 50 $\mu$m. Imaging was done on a CCD chip 1024×1280 pixels large. As evident from the magnified view (FIG. 9*b*) a sensor field of roughly 5 pixels was available for detecting the reflection spectrum.

Referring now to FIG. 10 in conclusion there is illustrated a spectrum obtained from 5 pixels, the transmission of the monochromator still being superposed in this case. The quality of these spectra indicates an accuracy of 2 $10^{-4}$ for detecting changes in the refractive index for 12,000 samples within a single measurement.

Although the invention has been described with respect to specific embodiments, these only serve to convey a better understanding to the skilled person and the present invention is not to be understood as being limited to these embodiments, but is defined by the appended claims, such that the present invention encompasses any device or method that falls into the scope or spirit of the claims and all of their equivalents. Reference signs also do not restrict the scope.

What is claimed is:

1. An SPR sensor array comprising a plurality of SPR sensor surface areas (120) arranged on a substrate (10, 20) in a two-dimensional matrix located in a plane to which the SPR sensor surface areas (120) are parallel and whereby radiation capable of exciting surface plasmons in the SPR sensor surface areas (120) under specific physical conditions can be guided through the substrate (10, 20) to be reflected from the SPR sensor surface areas, separating means (110) for separating each SPR sensor surface area (120) from its neighboring SPR sensor surface area (120), where the separating means (110) and SPR sensor surface areas (120) are provided such that at least outside of surface plasmon resonance occurring in the SPR sensor surface areas (120) the radiation (40) guided through the substrate (10, 20) is reflected in the region of the separating means to a different degree than in the region of the SPR sensor surface areas (120) to create a contrast between the separating means (110) and the SPR sensor surface areas (120) at least outside of surface plasmon resonance occurring in the SPR sensor surface areas (120) in the radiation reflected by the SPR sensor surface areas (120) and the separating means (110).

2. The SPR sensor array as set forth in claim 1 wherein the separating means (110) and the SPR sensor surface areas (120) are provided so that at least outside of surface plasmon resonance occurring in the SPR sensor surface areas (120) the radiation (40) guided through the substrate (10, 20) is reflected in the region of the separating means less strongly than in the region of the SPR sensor surface areas (120).

3. The SPR sensor array as set forth in claim 2 wherein the separating means (110) and the SPR sensor surface areas (120) are provided so that also on surface plasmon resonance occurring in the SPR sensor surface areas (120) the radiation (40) guided through the substrate (10, 20) is reflected in the region of the separating means less strongly than in the region of the SPR sensor surface areas (120).

4. The SPR sensor array as set forth in claim 1 wherein the separating means (110) comprises a contrast-forming material which is not SPR-compatible.

5. The SPR sensor array as set forth in claim 4 wherein the contrast-forming material is in direct contact with the substrate (10, 20).

6. The SPR sensor array as set forth in claim 4 wherein the contrast-forming material is an absorbing film of a metal, semiconductor material or polymer.

7. The SPR sensor array as set forth in claim 4 wherein the contrast-forming material has a refractive index in excess of or equal to the refractive index of the substrate (10, 20).

8. The SPR sensor array as set forth in claim 7 wherein the refractive index of the contrast-forming material is max. 0.1 higher than the refractive index of the substrate (10, 20).

9. The SPR sensor array as set forth in claim 7 wherein the thickness and width of a film composed of the contrast-forming material is defined so that a beam reflected from the substrate (10, 20) into the layer is reflected back to the substrate (10, 20) maximally twice by the side facing away from the surface of the substrate.

10. The SPR sensor array as set forth in claim 4 wherein the contrast-forming material is formulated with a material acting radiation-absorbing.

11. The SPR sensor array as set forth in claim 10 wherein the radiation-absorbing material is carbon or a dye.

12. The SPR sensor array as set forth in claim 1 wherein as regards the substrate surface the separating means (110) forms elevations (115, 116, 117) relative to the SPR sensor surface areas (120).

13. The SPR sensor array as set forth in claim 12 wherein the upper surface of the separating means (110) parallel to the substrate surface comprises a layer of the same SPR-compatible material as that covering the SPR sensor surface areas (120).

14. The SPR sensor array as set forth in claim 12 wherein the difference in thickness of the separating means (110) as compared to that of the SPR sensor surface areas (120) is in the range 0.05 to 5 mm.

15. The SPR sensor array as set forth in claim 12 wherein the flanks (112) of the separating means (110) surrounding each SPR sensor surface area (120) comprise a hydrophobic surface.

16. The SPR sensor array as set forth in claim 12 wherein the surface (118) of the separating means (110) parallel to the substrate surface comprises a hydrophobic surface.

17. The SPR sensor array as set forth in claim 1 wherein the substrate (10, 20) is a prism (20) of glass or plastic material.

18. The SPR sensor array as set forth in claim 1 wherein the substrate (10, 20) is a plate (10) of glass or plastic material.

19. The SPR sensor array as set forth in claim 18 wherein the plate (10) is attached to a prism (20).

20. The SPR sensor array as set forth in claim 19 wherein a refractive index matching film (30) is applied between the plate (10) and the prism (20).

21. The SPR sensor array as set forth in claim 20 wherein the refractive index matching film (30) is fluid and preferably comprises oleic acid.

22. The SPR sensor array as set forth in claim 21 wherein the SPR sensor array is configured so that the refractive index matching film (30) is filled by means of capillary action between the plate (10) and the prism (20).

23. The SPR sensor array as set forth in claim 18 wherein a well (150) is applied along the circumference of the plate (10, 100) so that a sample fluid (160) can be retained on the plate.

24. The SPR sensor array as set forth in claim 18 wherein provided on the plate (10, 100) are spacers (180) carrying a second plate (190) to form a capillary gap (170) which can be filled with sample fluid.

25. The SPR sensor array as set forth in claim 1 wherein in the plane at least 100, preferably 10000 sensor surface areas/$cm^2$ are provided.

26. The SPR sensor array as set forth in claim 1 wherein the SPR sensor surface areas are oval or circular in shape.

27. A measurement assembly for SPR measurements comprising a SPR sensor array as set forth in claim 1, irradiation means (405, 410, 420, 425, 430) for beaming the radiation capable of exciting surface plasmons in the SPR sensor surface areas (120) under specific physical conditions into the substrate (10, 20), means (600) for altering the physical conditions, and means (440, 450, 460, 490, 500) for detecting the radiation reflected from the SPR sensor array under the various physical conditions.

28. The measurement assembly as set forth in claim 27 wherein the specific physical conditions are a function of the angle of incidence of the radiation applied to the SPR sensor surface areas (120) and/or the wavelength of the radiation.

29. The measurement assembly as set forth in claim 27 wherein the SPR sensor array and the irradiation means (405, 410, 420, 425, 430) are configured so that the SPR sensor surface areas (120) of the SPR sensor array are irradiated and detected sequentially.

30. The measurement assembly as set forth in claim 29 comprising a beam controlling means in the irradiation means (405, 410, 420, 425, 430) for controlling a beam so that the SPR sensor surface areas (120) of the SPR sensor array are irradiated and detected sequentially.

31. The measurement assembly as set forth in claim 29 comprising a positioning table for two-dimensional positioning in the plane of the SPR sensor surface areas (120) which is controlled so that the SPR sensor surface areas (120) of the SPR sensor array are irradiated and detected sequentially.

32. The measurement assembly as set forth in claim 27 wherein the detecting means (440, 450, 460, 490, 500) comprises a detector for two-dimensional spatial resolution.

33. The measurement assembly as set forth in claim 32 wherein a positioning table for one-dimensional positioning in the plane of the SPR sensor surface areas (120) is provided for reading the two-dimensional matrix of the SPR sensor surface areas (120) line-by-line.

34. The measurement assembly as set forth in claim 32 wherein the measurement assembly is configured so that the SPR sensor surface areas (120) are irradiated simultaneously and the matrix of the SPR sensor surface areas (120) is imaged two-dimensionally on the spatial resolution detector.

35. The measurement assembly as set forth in claim 34 wherein the altering means (600) are configured so that the physical conditions are altered by changing the value of at least one physical parameter and that analyser means (600) are provided configured so that the value of the physical parameter is altered over a value range and an image (510) of the matrix of the SPR sensor surface areas (120) recorded for every change in the value of the physical parameter to obtain a reflectivity signal for each SPR sensor surface area (120).

36. The measurement assembly as set forth in claim 35 wherein imaging (510) is done on a pixel matrix and for each SPR sensor surface area (120) the reflectivity signal is obtained by forming the sum of the reflectivities over an image region (121) in relation to each SPR sensor surface area (120).

37. The measurement assembly as set forth in claim 36 wherein the imaging region (121) in relation to an SPR sensor surface area (120) comprises ten or more pixels, preferably five or less.

38. The measurement assembly as set forth in claim 35 wherein the physical parameter is the angle of incidence of the radiation on the SPR sensor surface areas (120) and/or the wavelength of the radiation.

39. The measurement assembly as set forth claim 32 wherein the irradiation means (405, 410, 420, 425, 430) comprises means (420, 425) for forming a beam of parallel radiation for illuminating the matrix of the SPR sensor surface areas (120) and the detecting means (440, 450, 460, 490, 500) comprising a telescopic element (440, 450) for imaging the radiation reflected from the SPR sensor array onto the detector.

40. The measurement assembly as set forth in claim 39 wherein the detector comprises a detection surface area which is tilted relative to the optical axis.

41. The measurement assembly as set forth in claim 40 wherein the matrix of the SPR sensor surface areas (120) is rectangular and has a larger matrix spacing in one direction than in the direction perpendicularly thereto to compensate the distortion in the image (510) at least in part, resulting from the large angle of incidence of the radiation on the sensor surface area.

42. The measurement assembly as set forth in claim 40 wherein the detecting means (440, 450, 460, 490, 500) comprises an anamorphotic lens (450) to compensate the distortion in the image (510) at least in part, resulting from tilting the detector surface area relative to the optical axis.

43. The measurement assembly as set forth in claim 32 wherein the detector comprises a CCD element.

44. An SPR sensor array comprising a plurality of SPR sensor surface areas (120) arranged on a substrate (10, 20) in a two-dimensional matrix located in a plane to which the SPR sensor surface areas (120) are parallel and whereby radiation capable of exciting surface plasmons in the SPR sensor surface areas (120) under specific physical conditions can be guided through the substrate (10, 20) to be reflected from the SPR sensor surface areas, separators (110) that separate each SPR sensor surface area (120) from a neighboring SPR sensor surface area (120), where the separators (110) and SPR sensor surface areas (120) are provided such that at least outside of surface plasmon resonance occurring in the SPR sensor surface areas (120) the radiation (40) guided through the substrate (10, 20) is reflected in the region of the separators to a different degree than in the region of the SPR sensor surface areas (120) to create a contrast between the separators (110) and the SPR sensor surface areas (120) at least outside of surface plasmon resonance occurring in the SPR sensor surface areas (120) in the radiation reflected by the SPR sensor surface areas (120) and the separators (110).

45. A measurement assembly for SPR measurements, comprising a SPR sensor array as set forth in claim 44, an irradiator (405, 410, 420, 425, 430) that beams the radiation capable of exciting surface plasmons in the SPR sensor surface areas (120) under specific physical conditions into the substrate (10, 20), an alterer (600) that alters the physical conditions, and a detector (440, 450, 460, 490, 500) that detects the radiation reflected from the SPR sensor array under the various physical conditions.

46. The SPR sensor array as set forth in claim 44 wherein the separators (110) and the SPR sensor surface areas (120) are provided so that at least outside of surface plasmon resonance occurring in the SPR sensor surface areas (120) the radiation (40) guided through the substrate (10, 20) is reflected in the region of the separators less strongly than in the region of the SPR sensor surface areas (120).

47. The SPR sensor array as set forth in claim 46 wherein the separators (110) and the SPR sensor surface areas (120) are provided so that also on surface plasmon resonance occurring in the SPR sensor surface areas (120) the radiation (40) guided through the substrate (10, 20) is reflected in the region of the separators less strongly than in the region of the SPR sensor surface areas (120).

48. The SPR sensor array as set forth in claim 44 wherein the separators (110) comprise a contrast-forming material which is not SPR-compatible.

49. The SPR sensor array as set forth in claim 48 wherein the contrast-forming material is in direct contact with the substrate (10, 20).

50. The SPR sensor array as set forth in claim 48 wherein the contrast-forming material is an absorbing film of a metal, semiconductor material or polymer.

51. The SPR sensor array as set forth in claim 48 wherein the contrast-forming material has a refractive index in excess of or equal to the refractive index of the substrate (10, 20).

52. The SPR sensor array as set forth in claim 51 wherein the refractive index of the contrast-forming material is at most 0.1 higher than the refractive index of the substrate (10, 20).

53. The SPR sensor array as set forth in claim 51 wherein the thickness and width of a film composed of the contrast-forming material is defined so that a beam reflected from the substrate (10, 20) into the layer is reflected back to the substrate (10, 20) at most twice by the side facing away from the surface of the substrate.

54. The SPR sensor array as set forth in claim 48 wherein the contrast-forming material is formulated with a material acting radiation-absorbing.

55. The SPR sensor array as set forth in claim 54 wherein the radiation-absorbing material is carbon or a dye.

56. The SPR sensor array as set forth in claim 44 wherein as regards the substrate surface the separators (110) form elevations (115, 116, 117) relative to the SPR sensor surface areas (120).

57. The SPR sensor array as set forth in claim 56 wherein the upper surface of the separators (110) parallel to the substrate surface comprise a layer of the same SPR-compatible material as that covering the SPR sensor surface areas (120).

58. The SPR sensor array as set forth in claim 56 wherein the difference in thickness of the separators (110) as compared to that of the SPR sensor surface areas (120) is in the range 0.05 to 5 mm.

59. The SPR sensor array as set forth in claim 56 wherein the flanks (112) of the separators (110) surrounding each SPR sensor surface area (120) comprise a hydrophobic surface.

60. The SPR sensor array as set forth in claim 56 wherein the surface (118) of the separators (110) parallel to the substrate surface comprises a hydrophobic surface.

61. The SPR sensor array as set forth in claim 44 wherein the substrate (10, 20) is a prism (20) of glass or plastic material.

62. The SPR sensor array as set forth in claim 44 wherein the substrate (10, 20) is a plate (10) of glass or plastic material.

63. The SPR sensor array as set forth in claim 62 wherein the plate (10) is attached to a prism (20).

64. The SPR sensor array as set forth in claim 63 wherein a refractive index matching film (30) is applied between the plate (10) and the prism (20).

65. The SPR sensor array as set forth in claim 64 wherein the refractive index matching film (30) is fluid and preferably comprises oleic acid.

66. The SPR sensor array as set forth in claim 65 wherein the SPR sensor array is configured so that the refractive index matching film (30) is filled by means of capillary action between the plate (10) and the prism (20).

67. The SPR sensor array as set forth in claim 62 wherein a well (150) is applied along the circumference of the plate (10, 100) so that a sample fluid (160) can be retained on the plate.

68. The SPR sensor array as set forth in claim 62 wherein provided on the plate (10, 100) are spacers (180) carrying a second plate (190) to form a capillary gap (170) which can be filled with sample fluid.

69. The SPR sensor array as set forth in claim 44 wherein in the plane at least 100, preferably 10000 sensor surface areas/$cm^2$ are provided.

70. The SPR sensor array as set forth in claim 44 wherein the SPR sensor surface areas are oval or circular in shape.

* * * * *